US00PP28169P3

(12) United States Plant Patent
Olesen

(10) Patent No.: US PP28,169 P3
(45) Date of Patent: Jul. 11, 2017

(54) COMPACT FLORIBUNDA PLANT NAMED 'POULCAS048'

(50) Latin Name: ***Rosa* hybrid**
Varietal Denomination: Poulcas048

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,273

(22) Filed: Aug. 20, 2015

(65) Prior Publication Data

US 2017/0055407 P1 Feb. 23, 2017

(51) Int. Cl.
*A01H 5/02* (2006.01)

(52) U.S. Cl.
USPC ..... Plt./151

(58) Field of Classification Search
USPC ..... Plt./151, 150
CPC ..... A01H 5/0222
See application file for complete search history.

(56) References Cited

PUBLICATIONS http://poulsenroser.dk/media/73065/CASTLE-2013_LR_Poulsen-Roser.pdf; 2012, 1 page.*

* cited by examiner

*Primary Examiner* — Kent L Bell

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas048'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulcas048', originated as a single seedling from the stated cross.

The new variety may be distinguished from its male pollen parent and female seed parent primarily by the following characteristics. The female seed parent has a climbing growth habit with red flowers, while the new variety has a compact habit with red flowers. The male pollen parent has large flowers up to 100 mm in diameter, while the new variety has smaller flowers up to 65 mm in diameter.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas048' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulcas048' was selected in the spring of 2008 by the inventor as a single plant from the progeny of the aforementioned hybridization.

Asexual reproduction of 'Poulcas048' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulcas048' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas048'.

Specifically illustrated in FIG. 1 of the drawings are open flowers, flower buds, flower petals detached, and exposed reproductive flower parts.

Figure 1:
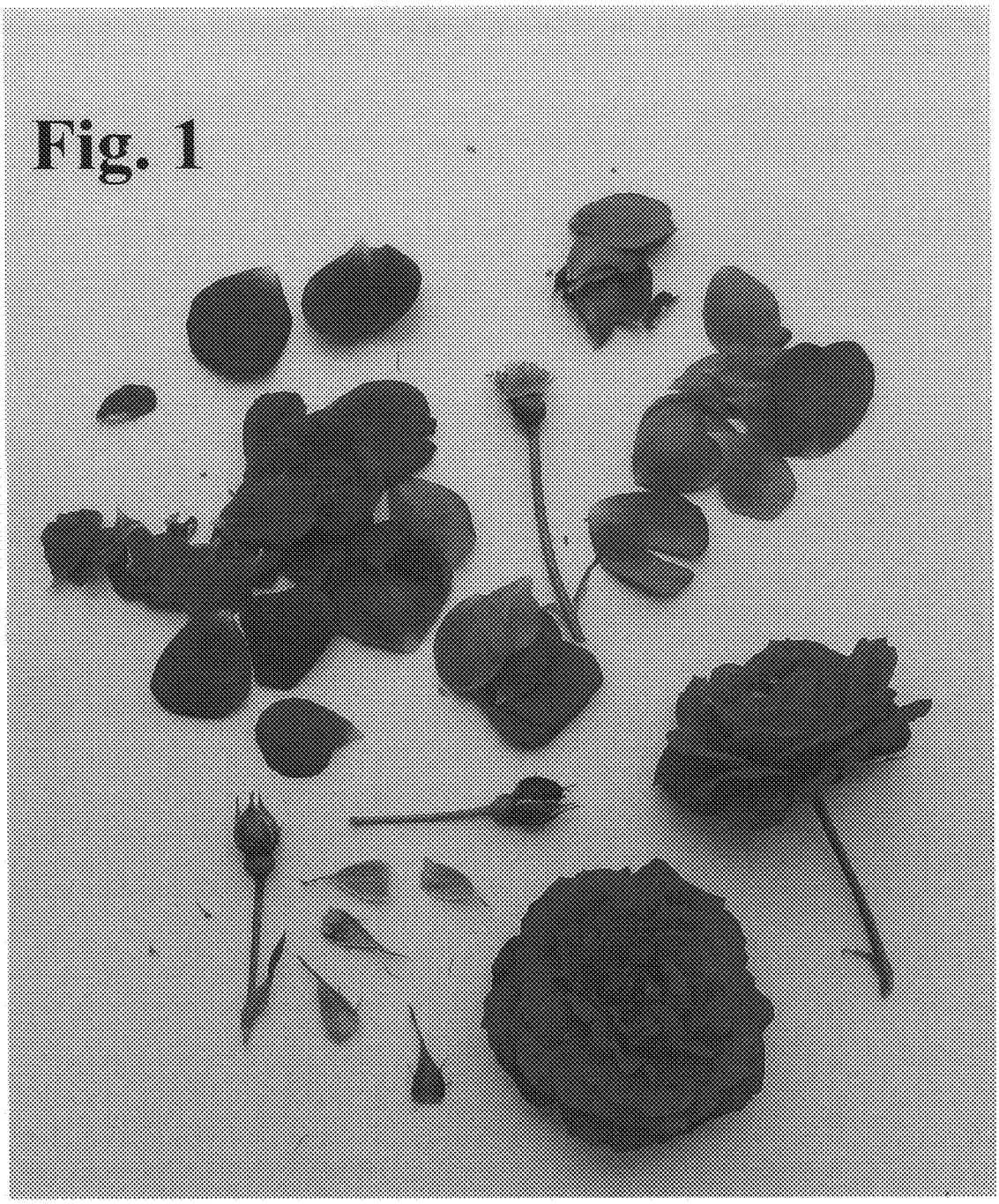
Figure 2:
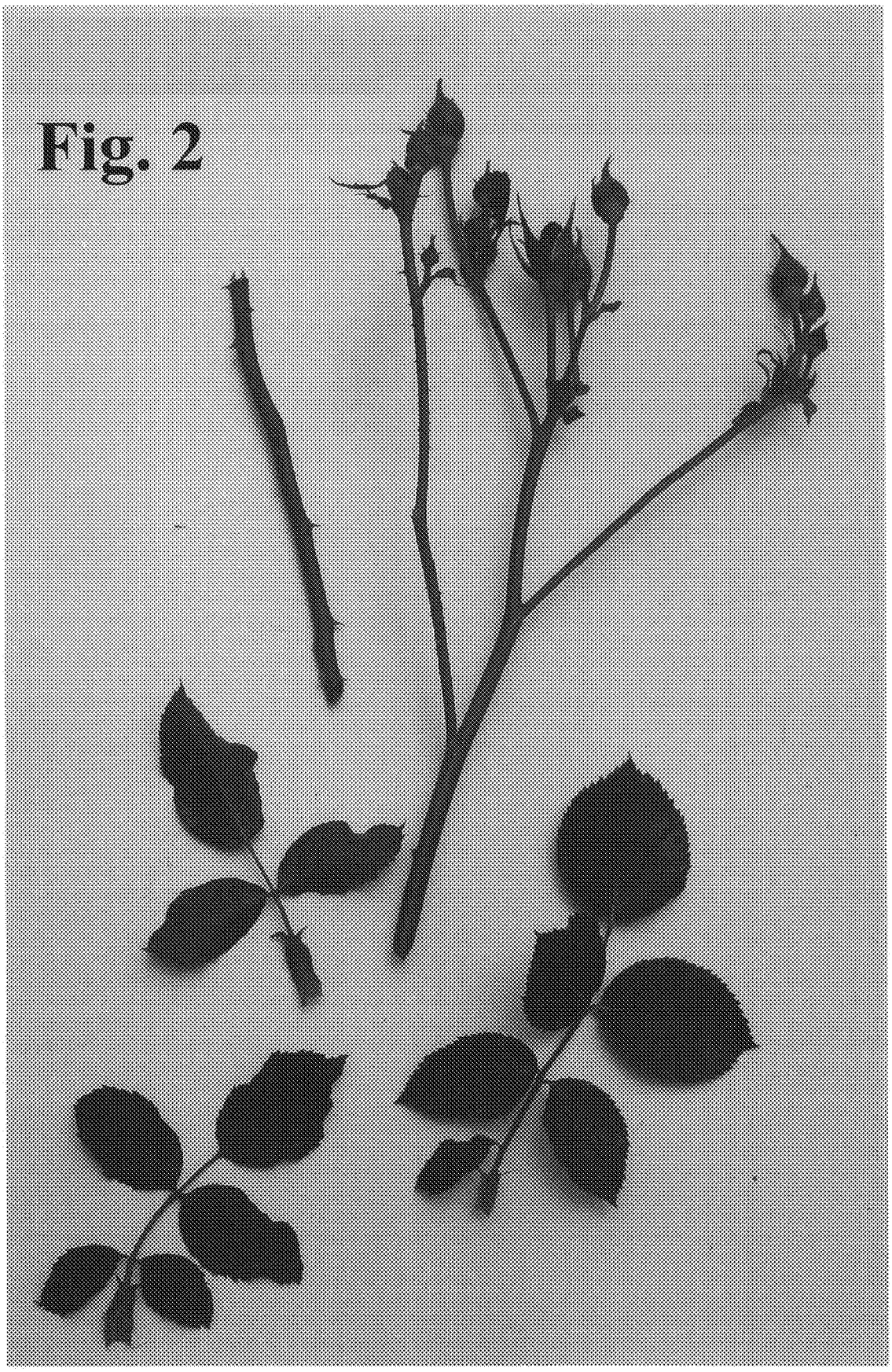

Specifically illustrated in FIG. 2 of the drawings are leaves, stems, and a cluster of flower buds on a branch. Plants shown are 2 years of age.

DETAILED DESCRIPTION OF THE VARIETY

The following is a description of 'Poulcas048', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety

'Poulander', U.S. Plant Pat. No. 6,265 are compared to 'Poulcas048' in the chart entitled Comparison with comparative cultivar 'Poulander'.

CHART 1

| | 'Poulcas048' | 'Poulander' |
|---|---|---|
| Petal Count | 85 | About 20 |
| Plant Height | 45 cm | 80 to 120 cm |
| General Tonality of Flower Color | Red Group 45B | Red Group 46B to 46C |

FLOWER AND FLOWER BUD

Blooming habit: Continuous.

Flower bud:

*Size*.—Upon opening, 20 mm in length from base of receptacle to end of bud. Bud diameter is 11 mm.

*Bud form*.—Urceolate.

*Bud color*.—As sepals divide petals are Greyed-Purple Group 187B.

*Sepal inner surface*.—Color: Yellow-Green Group 144B with weak anthocyanin Greyed-Red Group 180C. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—25 mm long, 5 mm wide.

*Receptacle*.—Texture: Smooth. Size: 5 mm in height, 8 mm wide. Color: Yellow-Green Group 144A with weak anthocyanin Greyed-Red Group 180C. Shape: Broadly elliptical.

*Pedicel*.—Surface: Smooth. Length: 30 mm. Diameter: 3 mm on average. Color: Yellow-Green Group 144A. Strength: Strong.

*Peduncle*.—Length: Varying in length from 3 to 12 cm. Diameter: About 3 to 4 mm. Color: Yellow-Green Group 144A. Texture: Smooth.

Flower bud development: Flower buds are borne in corymbs of 15 average flower buds per stem.

Flower bloom:

*Fragrance*.—Moderate spicy scent.

*Duration*.—The blooms have a duration on the plant of approximately 12 days. Petals fall cleanly away from plant after flowers have fully matured.

*Size*.—Flower diameter is 65 mm when open. Flower depth is 20 mm.

*Flower shape*.—Pompon shaped, rounded, very double, filled with masses of moderately sized petals.

*Shape of flower, side view*.—The upper portion is a flattened convex. The lower portion is concave.

Petalage: Under normal conditions, flowers have 85 petals total, 5 to 7 of which are petaloids.

General tonality of flower: Open flowers are Red Group 45B.

Petal color:

*Upon opening, outer petals*.—Upper surface: Red Group 45B. Lower surface: Red Group 53B.

*Upon opening, inner petals*.—Upper surface: Red Group 45B. Lower surface: Red Group 53B.

*Basal petal spots, upon opening*.—Upper surface: Yellow Group 4D. Lower surface: Yellow Group 4D.

*After opening, outer petals*.—Upper surface: Red Group 45B. Lower surface: Red Group 53B.

*After opening, inner petals*.—Upper surface: Red Group 45B. Lower surface: Red Group 53B.

*Basal petal spots, after opening*.—Upper surface: Yellow Group 4D. Lower surface: Yellow Group 4D.

Petals:

*Petal reflex*.—Strong reflex.

*Margin*.—Occasionally a cleft at the apex of the margin. Moderate undulations.

*Shape*.—Generally narrow ellipse. Apex shape: Rounded. Base shape: Acute.

*Size*.—Largest petals are about 30 mm (l)×25 mm (w).

*Texture*.—Smooth.

*Thickness*.—Average.

Petaloids:

*Size*.—10 mm (l) by 5 mm (w).

*Quantity*.—5 to 7.

*Shape*.—Asymmetric. The base is acute and the apex is rounded.

*Color*.—Red Group 45B upper surface, Red Group 53B lower surface with a petal spot Yellow Group 4D.

Reproductive flower parts:

*Pollen*.—None observed.

*Anthers*.—Size: 1 mm in length. Color: Greyed-Orange Group 164C. Quantity: 35 on average.

*Filaments*.—Color: Yellow-Orange Group 21B. Length: 4 mm.

*Pistils*.—Length: 7 mm. Quantity: 30 on average.

*Stigmas*.—Color: Yellow-White Group 158B.

*Styles*.—Color: Yellow-White Group 158B.

*Location of stigmas*.—Superior in location relative to the length of the filaments and the height of the anthers.

*Hips*.—None Observed.

PLANT

Plant growth: Upright, bushy. Plants are 45 cm in height, and 45 cm wide.

Stems:

*Color*.—Juvenile growth: Yellow-Green Group 144A. Mature growth: Yellow-Green Group 144A.

*Length*.—On average, canes are 25 cm from the base of the plant to the flowering portion.

*Diameter*.—About 6 mm.

*Internodes*.—On mature canes about 40 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 4 mm.

*Shape*.—Upper portion is linear. Lower portion is concave.

*Color*.—Juvenile prickles: Greyed-Red Group 179B. Mature prickles: Greyed-Red Group 179B.

Plant foliage:

*Compound leaf*.—140 mm (l)×85 (w).

*Quantity*.—2 leaves per 10 cm of stem on average.

*Color of juvenile foliage*.—Upper side: Yellow-Green Group 146B. Lower side: Yellow-Green Group 146B.

*Color of mature foliage*.—Upper side: Yellow-Green Group 147A. Lower side: Yellow-Green Group 147B.

Plant leaves and leaflets:

*Stipules*.—Size: 20 mm long, 6 mm wide. Quantity: 2 per compound leaf. Shape: Linear, slightly broad based with outward extending apices. Margins: Finely serrated. Color: Yellow-Green Group 144A.

*Petiole*.—Length: 35 mm. Diameter: 1.5 mm. Upper surface: Color: Yellow-Green Group 144B with light intonations of Greyed-Red Group 180C. Lower surface: Color: Yellow-Green Group 144A.

*Rachis*.—Length: 50 mm. Upper surface: Color: Yellow-Green Group 144B. Lower surface: Color: Yellow-Green Group 144A. Observations: Small prickles.

*Leaflet*.—Quantity: Normally 5 leaflets. Margins: Serrated. Size: On average terminal leaflets are 50 mm long, 38 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa,* rust *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas048', substantially as illustrated and described herein, due to its abundant red flowers, disease resistance, and extended period of bloom.

* * * * *